US007136450B2

(12) United States Patent
Ying et al.

(10) Patent No.: US 7,136,450 B2
(45) Date of Patent: Nov. 14, 2006

(54) METHOD OF AND SYSTEM FOR ADAPTIVE SCATTER CORRECTION IN MULTI-ENERGY COMPUTED TOMOGRAPHY

(75) Inventors: Zhengrong Ying, Wakefield, MA (US); Ram Naidu, Waban, MA (US); Sergey Simanovsky, Brookline, MA (US); Carl R. Crawford, Brookline, MA (US)

(73) Assignee: Analogic Corporation, Peabody, MA (US)

( * ) Notice: Subject to any disclaimer, the term of this patent is extended or adjusted under 35 U.S.C. 154(b) by 253 days.

(21) Appl. No.: 10/853,942

(22) Filed: May 26, 2004

(65) Prior Publication Data
US 2005/0276373 A1 Dec. 15, 2005

(51) Int. Cl.
*A61B 6/00* (2006.01)
(52) U.S. Cl. .......................................................... 378/7
(58) Field of Classification Search .................... 378/4, 378/7; 382/131, 261
See application file for complete search history.

(56) References Cited

U.S. PATENT DOCUMENTS

| 4,727,562 | A | * | 2/1988 | Belanger ................... 378/98.4 |
| 4,891,829 | A | * | 1/1990 | Deckman et al. .............. 378/4 |
| 5,802,134 | A | | 9/1998 | Larson et al. .................... 378/4 |
| 5,881,122 | A | | 3/1999 | Ruth et al. ........................ 378/4 |
| 5,887,047 | A | | 3/1999 | Ruth et al. ........................ 378/4 |
| 5,901,198 | A | | 5/1999 | Ruth et al. ...................... 378/57 |
| 5,909,477 | A | | 6/1999 | Ruth et al. ........................ 378/4 |
| 5,932,874 | A | | 8/1999 | Legg et al. ............. 250/231.13 |
| 5,937,028 | A | | 8/1999 | Tybinkowski et al. ...... 378/203 |
| 5,949,842 | A | | 9/1999 | Schafer et al. .................. 378/4 |
| 5,970,113 | A | | 10/1999 | Ruth et al. ...................... 378/19 |
| 5,982,843 | A | | 11/1999 | Bailey et al. .................... 378/4 |
| 5,982,844 | A | | 11/1999 | Tybinkowski et al. .......... 378/4 |
| 6,025,143 | A | | 2/2000 | Simanovsky et al. ........ 435/7.1 |
| 6,026,171 | A | | 2/2000 | Hiraoglu et al. ............. 382/100 |
| 6,035,014 | A | | 3/2000 | Hiraoglu et al. .............. 378/57 |
| 6,067,366 | A | | 5/2000 | Simanovsky et al. ....... 382/100 |
| 6,075,871 | A | | 6/2000 | Simanovsky et al. ....... 382/100 |
| 6,076,400 | A | | 6/2000 | Bechwati et al. ............. 73/433 |
| 6,078,642 | A | | 6/2000 | Simanovsky et al. ......... 378/57 |
| 6,091,795 | A | | 7/2000 | Schafer et al. ................ 378/19 |
| 6,108,396 | A | | 8/2000 | Bechwati et al. ............... 378/4 |
| 6,111,974 | A | | 8/2000 | Hiraoglu et al. ............. 382/100 |
| 6,128,365 | A | | 10/2000 | Bechwati et al. ............. 378/57 |
| 6,195,444 | B1 | | 2/2001 | Simanovsky et al. ....... 382/100 |
| 6,196,715 | B1 | * | 3/2001 | Nambu et al. .............. 378/197 |

(Continued)

*Primary Examiner*—Edward J. Glick
*Assistant Examiner*—Alexander Taningco
(74) *Attorney, Agent, or Firm*—McDermott Will & Emery LLP

(57) ABSTRACT

Method of and system for adaptive scatter correction in the absence of scatter detectors in multi-energy computed tomography are provided, wherein input projection data acquired using at least two x-ray spectra for scanned objects may include a set of low energy projections and a set of high energy projections; wherein a low-pass filter of variable size is provided; the method comprises estimating the size of the low-pass filter; computing amounts of scatter; and correcting both sets of projections for scatter. The estimation of low-pass filter size comprises thresholding high energy projections into binary projections; filtering the binary projections; finding the maximum of the filtered binary projections; calculating the low-pass filter size from the found maximum. The computation of amounts of scatter comprises exponentiating input projections; low-pass filtering the exponentiated projections with the estimated filter size; computing the amounts of scatter from the filtered projections.

14 Claims, 10 Drawing Sheets

U.S. PATENT DOCUMENTS

| | | |
|---|---|---|
| 6,256,404 B1 | 7/2001 | Gordon et al. ............... 382/131 |
| 6,272,230 B1 | 8/2001 | Hiraoglu et al. ............ 382/100 |
| 6,345,113 B1 | 2/2002 | Crawford et al. ........... 382/131 |
| 6,490,476 B1 * | 12/2002 | Townsend et al. .......... 600/427 |
| 6,618,466 B1 * | 9/2003 | Ning ........................... 378/62 |
| 6,687,326 B1 | 2/2004 | Bechwati et al. .............. 378/7 |
| 6,721,387 B1 | 4/2004 | Naidu et al. ................... 378/4 |

* cited by examiner

METHOD OF AND SYSTEM FOR ADAPTIVE SCATTER CORRECTION IN MULTI-ENERGY COMPUTED TOMOGRAPHY

RELATED APPLICATIONS

This patent application and/or patents are related to the following co-pending U.S. applications and/or issued U.S. patents, of the same assignee as the present application, the contents of which are incorporated herein in their entirety by reference:

"Nutating Slice CT Image Reconstruction Apparatus and Method," invented by Gregory L. Larson, et al., U.S. application Ser. No. 08/831,558, filed on Apr. 9, 1997, now U.S. Pat. No. 5,802,134, issued on Sep. 1, 1998;

"Computed Tomography Scanner Drive System and Bearing," invented by Andrew P. Tybinkowski, et al., U.S. application Ser. No. 08/948,930, filed on Oct. 10, 1997, now U.S. Pat. No. 5,982,844, issued on Nov. 9, 1999;

"Air Calibration Scan for Computed Tomography Scanner with Obstructing Objects," invented by David A. Schafer, et al., U.S. application Ser. No. 08/948,937, filed on Oct. 10, 1997, now U.S. Pat. No. 5,949,842, issued on Sep. 7, 1999;

"Computed Tomography Scanning Apparatus and Method With Temperature Compensation for Dark Current Offsets," invented by Christopher C. Ruth, et al., U.S. application Ser. No. 08/948,928, filed on Oct. 10, 1997, now U.S. Pat. No. 5,970,113, issued on Oct. 19, 1999;

"Computed Tomography Scanning Target Detection Using Non-Parallel Slices," invented by Christopher C. Ruth, et al., U.S. application Ser. No. 08/948,491, filed on Oct. 10, 1997, now U.S. Pat. No. 5,909,477, issued on Jun. 1, 1999;

"Computed Tomography Scanning Target Detection Using Target Surface Normals," invented by Christopher C. Ruth, et al., U.S. application Ser. No. 08/948,929, filed on Oct. 10, 1997, now U.S. Pat. No. 5,901,198, issued on May 4, 1999;

"Parallel Processing Architecture for Computed Tomography Scanning System Using Non-Parallel Slices," invented by Christopher C. Ruth, et al., U.S. application Ser. No. 08/948,697, filed on Oct. 10, 1997, U.S. Pat. No. 5,887,047, issued on Mar. 23, 1999;

"Computed Tomography Scanning Apparatus and Method For Generating Parallel Projections Using Non-Parallel Slice Data," invented by Christopher C. Ruth, et al., U.S. application Ser. No. 08/948,492, filed on Oct. 10, 1997, now U.S. Pat. No. 5,881,122, issued on Mar. 9, 1999;

"Computed Tomography Scanning Apparatus and Method Using Adaptive Reconstruction Window," invented by Bernard M. Gordon, et al., U.S. application Ser. No. 08/949,127, filed on Oct. 10, 1997, now U.S. Pat. No. 6,256,404, issued on Jul. 3, 2001;

"Area Detector Array for Computed Tomography Scanning System," invented by David A Schafer, et al., U.S. application Ser. No. 08/948,450, filed on Oct. 10, 1997, now U.S. Pat. No. 6,091,795, issued on Jul. 18, 2000;

"Closed Loop Air Conditioning System for a Computed Tomography Scanner," invented by Eric Bailey, et al., U.S. application Ser. No. 08/948,692, filed on Oct. 10, 1997, now U.S. Pat. No. 5,982,843, issued on Nov. 9, 1999;

"Measurement and Control System for Controlling System Functions as a Function of Rotational Parameters of a Rotating Device," invented by Geoffrey A. Legg, et al., U.S. application Ser. No. 08/948,493, filed on Oct. 10, 1997, now U.S. Pat. No. 5,932,874, issued on Aug. 3, 1999;

"Rotary Energy Shield for Computed Tomography Scanner," invented by Andrew P. Tybinkowski, et al., U.S. application Ser. No. 08/948,698, filed on Oct. 10, 1997, now U.S. Pat. No. 5,937,028, issued on Aug. 10, 1999;

"Apparatus and Method for Detecting Sheet Objects in Computed Tomography Data," invented by Muzaffer Hiraoglu, et al., U.S. application Ser. No. 09/022,189, filed on Feb. 11, 1998, now U.S. Pat. No. 6,111,974, issued on Aug. 29, 2000;

"Apparatus and Method for Eroding Objects in Computed Tomography Data," invented by Sergey Simanovsky, et al., U.S. application Ser. No. 09/021,781, filed on Feb. 11, 1998, now U.S. Pat. No. 6,075,871, issued on Jun. 13, 2000;

"Apparatus and Method for Combining Related Objects in Computed Tomography Data," invented by Ibrahim M. Bechwati, et al., U.S. application Ser. No. 09/022,060, filed on Feb. 11, 1998, now U.S. Pat. No. 6,128,365, issued on Oct. 3, 2000;

"Apparatus and Method for Detecting Sheet Objects in Computed Tomography Data," invented by Sergey Simanovsky, et al., U.S. application Ser. No. 09/022,165, filed on Feb. 11, 1998, now U.S. Pat. No. 6,025,143, issued on Feb. 15, 2000;

"Apparatus and Method for Classifying Objects in Computed Tomography Data Using Density Dependent Mass Thresholds," invented by Ibrahim M. Bechwati, et al., U.S. application Ser. No. 09/021,782, filed on Feb. 11, 1998, now U.S. Pat. No. 6,076,400, issued on Jun. 20, 2000;

"Apparatus and Method for Correcting Object Density in Computed Tomography Data," invented by Ibrahim M. Bechwati, et al., U.S. application Ser. No. 09/022,354, filed on Feb. 11, 1998, now U.S. Pat. No. 6,108,396, issued on Aug. 22, 2000;

"Apparatus and Method for Density Discrimination of Objects in Computed Tomography Data Using Multiple Density Ranges," invented by Sergey Simanovsky, et al., U.S. application Ser. No. 09/021,889, filed on Feb. 11, 1998, now U.S. Pat. No. 6,078,642, issued on Jun. 20, 2000;

"Apparatus and Method for Detection of Liquids in Computed Tomography Data," invented by Muzaffer Hiraoglu, et al., U.S. application Ser. No. 09/022,064, filed on Feb. 11, 1998, now U.S. Pat. No. 6,026,171, issued on Feb. 15, 2000;

"Apparatus and Method for Optimizing Detection of Objects in Computed Tomography Data," invented by Muzaffer Hiraoglu, et al., U.S. application Ser. No. 09/022,062, filed on Feb. 11, 1998, now U.S. Pat. No. 6,272,230, issued on Aug. 7, 2001;

"Multiple-Stage Apparatus and Method for Detecting Objects in Computed Tomography Data," invented by Muzaffer Hiraoglu, et al., U.S. application Ser. No. 09/022,164, filed on Feb. 11, 1998, now U.S. Pat. No. 6,035,014, issued on Mar. 7, 2000;

"Apparatus and Method for Detecting Objects in Computed Tomography Data Using Erosion and Dilation of Objects," invented by Sergey Simanovsky, et al., U.S. application Ser. No. 09/022,204, filed on Feb. 11, 1998, now U.S. Pat. No. 6,067,366, issued on May 23, 2000;

"Apparatus and method for processing object data in computed tomography data using object projections," invented by Carl R. Crawford, et al, U.S. application Ser. No. 09/228379, filed on Jan. 12, 1999, now U.S. Pat. No. 6,345,113, issued on Feb. 5, 2002;

"Apparatus and method for detecting concealed objects in computed tomography data," invented by Sergey Simanovsky, et al., U.S. application Ser. No. 09/228,380, filed on Jan. 12, 1999, now U.S. Pat. No. 6,195,444, issued on Feb. 27, 2001;

"Method of and system for correcting scatter in a computed tomography scanner," invented by Ibrahim M. Bechwati, et al, U.S. application Ser. No. 10/121,466, filed on Apr. 11, 2002, now U.S. Pat. No. 6,687,326, issued on Feb. 3, 2004;

"Method of and system for reducing metal artifacts in images generated by x-ray scanning devices," invented by Ram Naidu, et al, U.S. application Ser. No. 10/171,116, filed on Jun. 13, 2002, now U.S. Pat. No. 6,721,387, issued on Apr. 13, 2004;

"Decomposition of Multi-Energy Scan Projections using Multi-Step Fitting," invented by Ram Naidu, et al, U.S. application Ser. No. 10/611,572, filed on Jul. 1, 2003;

"Method of and system for computing effective atomic number image in multi-energy computed tomography," invented by Zhengrong Ying, et al, U.S. application Ser. No. 10/850,910, filed on May 21, 2004;

FIELD OF THE DISCLOSURE

The present disclosure relates to systems and methods for processing projection data in a computed tomography scanner, and more particularly to a method of and system for adaptive scatter correction in the absence of scatter detectors for the projection data in a multi-energy computed tomography scanner.

BACKGROUND OF THE DISCLOSURE

Various X-ray baggage scanning systems are known for detecting the presence of explosives and other prohibited items in baggage, or luggage, prior to loading the baggage onto a commercial aircraft. A common technique of measuring a material's density is to expose the material to X-rays and to measure the amount of radiation absorbed by the material, the absorption being indicative of the density. Since many explosive materials may be characterized by a range of densities differentiable from that of other items typically found in baggage, explosives are generally amenable to detection by X-ray equipment.

Most X-ray baggage scanning systems in use today are of the "line scanner" type and include a stationary X-ray source, a stationary linear detector array, and a conveyor belt for transporting baggage between the source and detector array as the baggage passes through the scanner. The X-ray source generates an X-ray beam that passes through and is partially attenuated by the baggage and is then received by the detector array. During each measuring interval the detector array generates data representative of the integral of density of the planar segment of the baggage through which the X-ray beam passes, and this data is used to form one or more raster lines of a two-dimensional image. As the conveyor belt transports the baggage past the stationary source and detector array, the scanner generates a two-dimensional image representative of the density of the baggage, as viewed by the stationary detector array. The density image is typically displayed for analysis by a human operator.

Techniques using dual energy X-ray sources are known for providing additional information about a material's characteristics, beyond solely a density measurement. Techniques using dual energy X-ray sources involve measuring the X-ray absorption characteristics of a material for two different energy levels of X-rays. Depending upon the calibration of the scanner, dual energy measurements provide an indication of dual parameters of the material being scanned. For example, at one calibration setting, the dual parameters can be chosen to be the material's effective atomic number (Z is denoted as "effective atomic number") and the material's density. At another calibration setting, the dual parameters can be chosen to be the material's Photoelectric coefficients and the material's Compton coefficients. At yet another calibration setting, the dual parameters can be chosen to be an amount of a first material present (e.g., plastic) and an amount of a second material present (e.g., aluminum). Dual energy X-ray techniques for energy-selective reconstruction of X-ray Computer Tomography (hereinafter referred to as CT) images are described, for example, in Robert E. Alvarez and Albert Macovski, "Energy-selective Reconstructions in X-ray Computerized Tomography," Phys. Med. Biol. 1976, Vol. 21, No. 5, 733–744; and U.S. Pat. Nos. 4,029,963 and 5,132,998. One algorithm used to generate such dual parameters from dual energy X-ray projection data is known as the Alvarez/Macovski Algorithm (hereinafter referred to as AMA). Others are known in the art.

One proposed use for such dual energy techniques has been in connection with a baggage scanner for detecting the presence of explosives in baggage. Explosive materials are generally characterized by a known range of atomic numbers and are therefore amenable to detection by such dual energy X-ray sources. One such dual energy source is described in U.S. Pat. No. 5,661,774, entitled "Improved Dual Energy Power Supply," assigned to the present assignee and incorporated by reference. Other dual energy sources are known in the art.

Most explosives capable of significantly damaging an aircraft are sufficiently large in length, width, and height so as to be readily detectable by an X-ray scanner system regardless of the explosive's orientation within the baggage. Plastic explosives, however, present a particular challenge to baggage scanning systems. Due to their moldable nature, plastic explosives may be formed into geometric shapes that are difficult to detect. A plastic explosive powerful enough to damage an aircraft may be formed into a relatively thin sheet that is extremely small in one dimension and is relatively large in the other two dimensions. The detection of plastic explosives may be difficult because it may be difficult to see the explosive material in the image, particularly when the material is disposed so that the thin sheet is parallel to the direction of the X-ray beam as the sheet passes through the system.

Thus, detection of suspected baggage requires very attentive operators. The requirement for such attentiveness can result in greater operator fatigue, and fatigue as well as any distractions can result in a suspected bag passing through the system undetected. Accordingly, a great deal of effort has been made to design a better baggage scanner. Such designs, for example, have been described in U.S. Pat. No. 4,759,047 (Donges et al.); U.S. Pat. No. 4,884,289 (Glockmann et al.); U.S. Pat. No. 5,132,988 (Tsutsui et al.); U.S. Pat. No. 5,182,764 (Peschmann et al.); U.S. Pat. No. 5,247,561 (Kotowski); U.S. Pat. No. 5,319,547 (Krug et al.); U.S. Pat. No. 5,367,552 (Peschmann et al.); U.S. Pat. No. 5,490,218 (Krug et al.) and German Offenlegungsschrift DE 31 503 06 Al (Heimann GmbH).

At least one of these designs, described in U.S. Pat. No. 5,182,764 (Peschmann et al.) and U.S. Pat. No. 5,367,552 (Peschmann et al.) (hereinafter the '764 and '552 patents), has been commercially developed and is referred to hereinafter as the "Invision Machine." The Invision Machine includes a CT scanner of the third generation type, which typically includes an X-ray source and an X-ray detector system secured respectively to diametrically opposite sides of an annular-shaped platform or disk. The disk is rotatably mounted within a gantry support so that in operation the disk continuously rotates about a rotation axis while X-rays pass from the source through an object positioned within the opening of the disk to the detector system.

The detector system can include a linear or two-dimensional array of detectors disposed as a single row or multiple rows in the shape of a circular, cylindrical or spherical arc having a center of curvature at the focal spot of the X-ray source, i.e., the point within the X-ray source from which the X-rays emanate. The X-ray source generates a fan or pyramidal shaped beam, or fan or cone beam, of X-rays that emanates from the focal spot, passes through a planar imaging field, and is received by the detectors. The CT scanner includes a coordinate system defined by X-, Y- and Z-axes, wherein the axes intersect and are all normal to one another at the center of rotation of the disk as the disk rotates about the rotation axis. This center of rotation is commonly referred to as the "isocenter." The Z-axis is defined by the rotation axis and the X- and Y-axes are defined by and lie within the planar imaging field. The fan beam is thus defined as the volume of space defined between a point source, i.e., the focal spot, and the receiving surfaces of the detectors of the detector array exposed to the X-ray beam. Because the dimension of the receiving surfaces of each of the detectors of the array of detectors is relatively small in the Z-axis direction the beam is designed to be relatively thin in the Z-axis direction. Each detector generates an output signal representative of the intensity of the X-rays incident on that detector. Since the X-rays are partially attenuated by all the mass in their path, the output signal generated by each detector is representative of the density of all the mass disposed in the imaging field between the X-ray source and that detector.

As the disk rotates, the detector array is periodically sampled, and for each measuring interval each of the detectors in the detector array generates an output signal representative of the density of a portion of the object being scanned during that interval. The collection of all of the output signals generated by all the detectors of the detector array for any measuring interval is referred to as a "projection," or equivalently as a "view," and the angular orientation of the disk (and the corresponding angular orientations of the X-ray source and the detector array) during generation of a projection is referred to as the "projection angle." At each projection angle, the path of the X-rays from the focal spot to each detector, called a "ray," increases in cross section from an appropriate point source to the receiving surface area of the detector, and thus is thought to magnify the density measurement because the receiving surface area of the detector area is larger than any cross sectional area of the object through which the ray passes.

As the disk rotates around the object being scanned, the scanner generates a plurality of projections at a corresponding plurality of projection angles. Using well known algorithms a CT image of the object may be generated from all the projection data collected at each of the projection angles. The CT image is representative of the density of a two dimensional "slice" of the object through which the fan beam has passed during the rotation of the disk through the various projection angles. The resolution of the CT image is determined in part by the width of the receiving surface area of each detector in the plane of the beam, the width of the detector being defined herein as the dimension measured in the same direction as the width of the beam, while the length of the detector is defined herein as the dimension measured in a direction normal to the beam parallel to the rotation or Z-axis of the scanner. In general, the resolution of the CT image is inversely proportional to the width of the receiving surface of each detector in the plane of the fan beam.

Referring to the drawings, FIGS. 1, 2 and 3 show perspective, end cross-sectional and radial cross-sectional views, respectively, of a typical baggage scanning system 100, which includes a conveyor system 110 for continuously conveying baggage or luggage 112 in a direction indicated by arrow 114 through a central aperture of a CT scanning system 120. The conveyor system includes motor driven belts for supporting the baggage. Conveyer system 110 is illustrated as including a plurality of individual conveyor sections 122; however, other forms of conveyor systems may be used.

The CT scanning system 120 includes an annular shaped rotating platform, or disk, 124 disposed within a gantry support 125 for rotation about a rotation axis 127 (shown in FIG. 3) that is preferably parallel to the direction of travel 114 of the baggage 112. Disk 124 is driven about rotation axis 127 by any suitable drive mechanism, such as a belt 116 and motor drive system 118, or other suitable drive mechanism, such as the one described in U.S. Pat. No. 5,473,657 issued Dec. 5, 1995 to Gilbert McKenna, entitled "X-ray Tomographic Scanning System," which is assigned to the present assignee and which is incorporated herein in its entirety by reference. Rotating platform 124 defines a central aperture 126 through which conveyor system 110 transports the baggage 112.

The system 120 includes an X-ray tube 128 and a detector array 130 which are disposed on diametrically opposite sides of the platform 124. The detector array 130 can be a two-dimensional array such as the array described in U.S. Pat. No. 6,091,795 entitled, "Area Detector Array for Computed Tomography Scanning System." The system 120 further includes a data acquisition system (DAS) 134 for receiving and processing signals generated by detector array 130, and an X-ray tube control system 136 for supplying power to, and otherwise controlling the operation of, X-ray tube 128. The system 120 is also preferably provided with a computerized system (not shown) for processing the output of the data acquisition system 134 and for generating the necessary signals for operating and controlling the system 120. The computerized system can also include a monitor for displaying information including generated images. System 120 also includes shields 138, which may be fabricated from lead, for example, for preventing radiation from propagating beyond gantry 125.

The X-ray tube 128 may generate a pyramidally shaped beam, often referred to as a "cone beam," 132 of X-rays that pass through a three dimensional imaging field, through which conveying system 110 transports baggage 112. After passing through the baggage disposed in the imaging field, detector array 130 receives cone beam 132 and generates signals representative of the densities of exposed portions of baggage 112. The beam therefore defines a scanning volume of space. Platform 124 rotates about its rotation axis 127, thereby transporting X-ray source 128 and detector array 130 in circular trajectories about baggage 112 as the conveyor system 110 continuously transports baggage through central aperture 126, so as to generate a plurality of projections at a corresponding plurality of projection angles. When dual energy scanning mode is configured, the control system 136 supplies modulated high voltages with respect to alternating projection angles to the X-ray tube 128. The detector array 130 then receives data corresponding to high energy and low energy X-ray spectra in alternating projection angles.

Post-reconstruction analysis and pre-reconstruction analysis are the two prior art techniques generally recognized for using dual energy X-ray sources in materials analysis (e.g., in a baggage scanner for detecting the presence of explosives in baggage). In post-reconstruction analysis, the signal flow is as shown in FIG. 4. The scanner 120 is typically similar to the one shown in FIG. 1 and has an X-ray source capable of producing a fan beam at two distinct energy levels (i.e., dual energy). The DAS 134 gathers signals generated by detector array 130 at discrete angular positions of the rotating platform 124, and passes the signals to the pre-processing unit 206. The pre-processing unit 206 re-sorts the data it receives from the DAS 134 in order to optimize the sequence for the subsequent mathematical processing. The pre-processing unit 206 also corrects the data from the DAS 134 for detector temperature, intensity of the primary beam, gain and offset, and other deterministic error factors. Finally, the pre-processing unit 206 extracts data corresponding to high-energy views and routes it to a high energy path 208, and routes the data corresponding to low-energy views to a low energy path 210. A first reconstruction computer 218 receives the projection data from the high-energy path 208 and generates a CT image $I_H$ 226 corresponding to the high-energy series of projections. A second reconstruction computer 220 receives the projection data from the low-energy path 210 and generates a CT image $I_L$ 224 corresponding to the low-energy series of projections. A post-processing unit 230 receives the high energy CT image 226 and the low-energy CT image 224 and performs a voxel-by-voxel processing to yield a Z (effective atomic number) image $I_z$ 232. The Z image 232 and the high energy CT image 226 can be provided to operators on a display 240, and both images can be used for automatic explosive detection in 238 as well. The images from the post-reconstruction analysis usually do not yield accurate estimates of the material's effective atomic number, and suffer low SNR (Signal to Noise Ratio) and many artifacts as well.

In pre-reconstruction analysis, the signal flow is as shown in FIG. 5. As is described herein for pre-reconstruction analysis, the dual energy decomposition computer 212 receives the projection data on the high energy path 208 and the low energy path 210 and performs Alvarez/Macovski Algorithm to produce a first stream of projection data $A_c$ 214 which is dependent on a first parameter of the material being scanned and a second stream of projection data $A_p$ 216 which is dependent on a second parameter of the material scanned. The first material parameter is often the Compton coefficient $a_c$ and the second material parameter is often the photoelectric coefficient $a_p$. A first reconstruction computer 219 receives the first stream of projection data 214 and generates a Compton image $I_c$ 227 from the series of projections corresponding to the first material parameter. A second reconstruction computer 221 receives the second stream of projection data 216 and generates a photoelectric image $I_p$ 225 from the series projections corresponding to the second material parameter. The third reconstruction computer 218 receives the stream of projection data 208 and generates a CT image $I_H$ 226. The two images 225 and 227 are processed in the post-processing unit 230 to yield a Z image $I_z$ 232. The CT image 226 and the Z image 232 can be provided to operators on a display 240, and both images can be used for automatic explosive detection in 238 as well. The pre-reconstruction analysis yields better estimates of material's effective atomic than the post-reconstruction analysis. However the pre-reconstruction analysis requires one more reconstruction computers than the post-reconstruction analysis.

Various approaches have been used for decomposition of the input projection data $P_L$ and $P_H$ into Compton projections $A_c$ and photoelectric projections $A_p$. For example, the AMA method approximates $P_L$ and $P_H$ using polynomial functions in terms of the $A_c$ and $A_p$. The coefficients of the polynomial functions are determined through a calibration procedure as follows. By measuring the projections values of the combination of various thicknesses of two known materials, the coefficients can be calculated through a polynomial least squares fitting between the measured and modeled $P_L$ and $P_H$. Once the coefficients the polynomial functions are determined, the decomposition of the Compton and Photoelectric projections $A_c$ and $A_p$ from projections $P_L$ and $P_H$ is solved using the Newton-Raphson method.

Another prior art method of performing decomposition is the direct approximation method, discussed in L. A. Lehmann, R. E. Alvarez, A. Macovski, W. R. Brody, N. J. Pelc, S. J. Riederer, and A. L. Hall, *Generalized Image Combinations In Dual KVP Digital Radiography*, Med. Phys. 8, 659–667 (1981). In the direct approximation method, $A_c$ and $A_p$ are approximated as polynomial functions in terms of $P_L$ and $P_H$. The coefficients of the polynomial functions in the direct approximation method are determined through a calibration procedure by measuring the projections values of the combination of various thicknesses of two known materials.

In yet another prior art method, decomposition is accomplished using iso-transmission lines, described K. Chuang and H. K. Huang, *A Fast Dual-Energy Computational Method Using Isotransmission Lines and Tables*, Med. Phys. 14, 186–192 (1987). According to this method, for a given projection value, an iso-transmission line is represented by a linear equation in two basis functions. The iso-transmission line method requires a large amount of calibration data. Further, the iso-transmission lines become increasingly non-linear as the projection value increases. In such a situation, the linear equations are not valid and the method causes large approximation errors.

The pre-reconstruction analysis usually yields better estimates of the material's effective atomic number than the post-reconstruction analysis. However, the pre-reconstruction analysis as shown in FIG. 5 requires one more reconstruction computer than the post-reconstruction analysis as shown in FIG. 4. Note that the reconstruction computers are the most expensive parts among all the subsystems for processing projection data from DAS 134 to post-processing 230.

The effective atomic number (Z) is the estimate of the hypothetical single element that will give the same X-ray attenuation as the substance being evaluated. In the pre-reconstruction analysis, the Z images are derived from reconstructed Compton images and photoelectric images with the pre-reconstruction dual energy decomposition algorithms, such as in AMA method.

The detectors described before measure all the received photons including primary photons and scattered photons. Primary photons are the x-ray photons which travel from the x-ray source to the detectors through scanned objects along straight lines; and x-ray scatter is referred to the x-ray photons received in the detectors other than the primary photons. The x-ray scatter is mostly from elastic scattering and Compton scattering.

Elastic scattering results from the interaction of photons of an x-ray beam with atoms of a scanned object. The x-ray photons cause electrons of the scanned object to vibrate while still bound to their orbits around the nuclei. The electrons re-radiate the x-ray energy in all directions. The amount of scatter depends on the atomic number of the impinged atom. Generally, scatter increases with increasing atomic number. Compton scattering is due to the direct exchange of energy between the x-ray photon and an electron with which it collides. Part of the photon energy is absorbed by the electron and converted into kinetic energy. The photon is then scattered at a lower energy level. While most of the photons are attenuated within the scanned object, a small portion of photons are not absorbed, resulting in an increase in x-ray scatter received by the detectors.

Scatter causes artifacts in images reconstructed from the x-ray CT scanners. It adversely affects image contrast and generates streaks from high-density objects. The increase in x-ray intensity due to scatter reduces the measured densities, resulting in reduced contrast of scanned objects in the reconstructed images. Scatter also causes cupping and blurring similar to the beam hardening artifact in large bulk objects. In dual energy CT scanners, the above mentioned artifacts caused by scatter are amplified by the dual energy decomposition procedure, resulting in degraded quality on the Z (effective atomic number) image.

An exact solution to the problems caused by scatter cannot be determined due to the randomness of the scattering process. Some prior art systems utilize anti-scatter plates which are disposed between the detectors of a detector array and which act to reduce the amount of scatter that reaches each detector, so that the detector receives mostly x-rays that travel to the detector in a direction substantially perpendicular to the detector. However, anti-scatter plates are extremely expensive and add structural complexity to the Even with anti-scatter plates, scatter still exists due to misalignment of the anti-scanners. scatter plates and finite height of the anti-scatter plates.

Other prior art approaches for reducing scatter artifacts include estimating the amount of scatter and compensate for it. One of such approaches is shown in U.S. Pat. No. 6,687,326 (Bechwati et al.), assigned to the present assignee and incorporated here by reference. It uses additional detectors called scatter detectors to measure the amount of scatter. These scatter detectors are usually installed close to the main x-ray detectors used to detect CT projection data. When the x-ray detector array has many rows of detectors, the scatter detectors can not be placed close enough to yield accurate measurement of the amount of scatter.

Other prior art approaches for estimating amounts of scatter without scatter detectors include using constant scatter values, such as described in G. H. Glover, *Compton Scatter Effects in CT Reconstructions*, Medical Physics Vo. 9, No. 6, Nov/Dec 1982, pp. 860–867. However scattering is a complicated, spatially-correlated process, and using a constant scatter value for all the detectors is not accurate enough for the generation of Z images in multi-energy CT scanners.

SUMMARY OF THE DISCLOSURE

In accordance with one aspect of the disclosure, an adaptive scatter correction algorithm for multi-energy projections is provided to better estimate amounts of scatter and correct for them, resulting in improved quality of Z (effective atomic number) images. The algorithm does not use scatter detectors to measure the amounts of scatter. Instead, it estimates amounts of scatter from the input projection data. The algorithm takes the spatial correlation of the scattering process into account, and adaptively uses attenuations and shapes of scanned objects to estimate amounts of scatter.

In accordance with one aspect of the disclosure, the input projection data may include a set of low energy projections and a set of high energy projections acquired by scanning a set of objects using at least two x-ray spectra.

In accordance with one aspect of the disclosure, a low-pass filter of variable size is used to compute amounts of scatter contained in the projection data. In one embodiment, a one-dimensional odd-number-point long rectangular filter may be used. Alternatively, two-dimensional and three-dimensional low-pass filters can be used to include scatter estimation along the detector row and along the view angle dimensions. Other types of low-pass filters besides the rectangular low-pass filter can be used, such as Hanning, Hamming, Kaiser, and Gaussian low-pass filters.

In one embodiment of the disclosure, the algorithm estimates the necessary size of the low-pass filter, which adapts to sizes and attenuations of scanned objects. The low-pass filter size is estimated using the set of high energy projections. Alternatively, the low energy projections can also be used to estimate the low-pass filter size.

In one embodiment of the disclosure, the estimation of the low-pass filter size may include thresholding the high energy projections, filtering the binary projections, calculating the filter size, and clamping the calculated filter size.

In one embodiment of the disclosure, the low-pass filter of the estimated size is used to compute amounts of scatter for both sets of projections. The filtered projections are preferably multiplied with the projections themselves and scaling factors to yield the estimated amounts of scatter. In accordance with one aspect of the disclosure, the scaling factor for the low energy projections may be larger than that for the high energy projections. In another embodiment, filtering the projections in estimating the amounts of scatter may include exponentiating the input projections.

In one embodiment of the disclosure, the computed amounts of scatter may be subtracted from the input projections to yield scatter corrected projections.

BRIEF DESCRIPTION OF THE DRAWINGS

The drawing figures depict preferred embodiments by way of example, not by way of limitations. In the figures, like reference numerals refer to the same or similar elements.

DETAILED DESCRIPTION OF THE PREFERRED EMBODIMENTS

In accordance with the disclosure, an adaptive scatter correction algorithm for multi-energy projections is provided to better estimate amounts of scatter and correct for them, resulting in improved quality of Z (effective atomic number) images. The algorithm does not use scatter detectors to measure the amounts of scatter, but instead, estimates the amounts of scatter from the input projection data. The algorithm preferably takes the spatial correlation of the scattering process into account, and adaptively uses attenuations and shapes of scanned objects to estimate the amounts of scatter, thereafter correcting for them.

Figure 1:
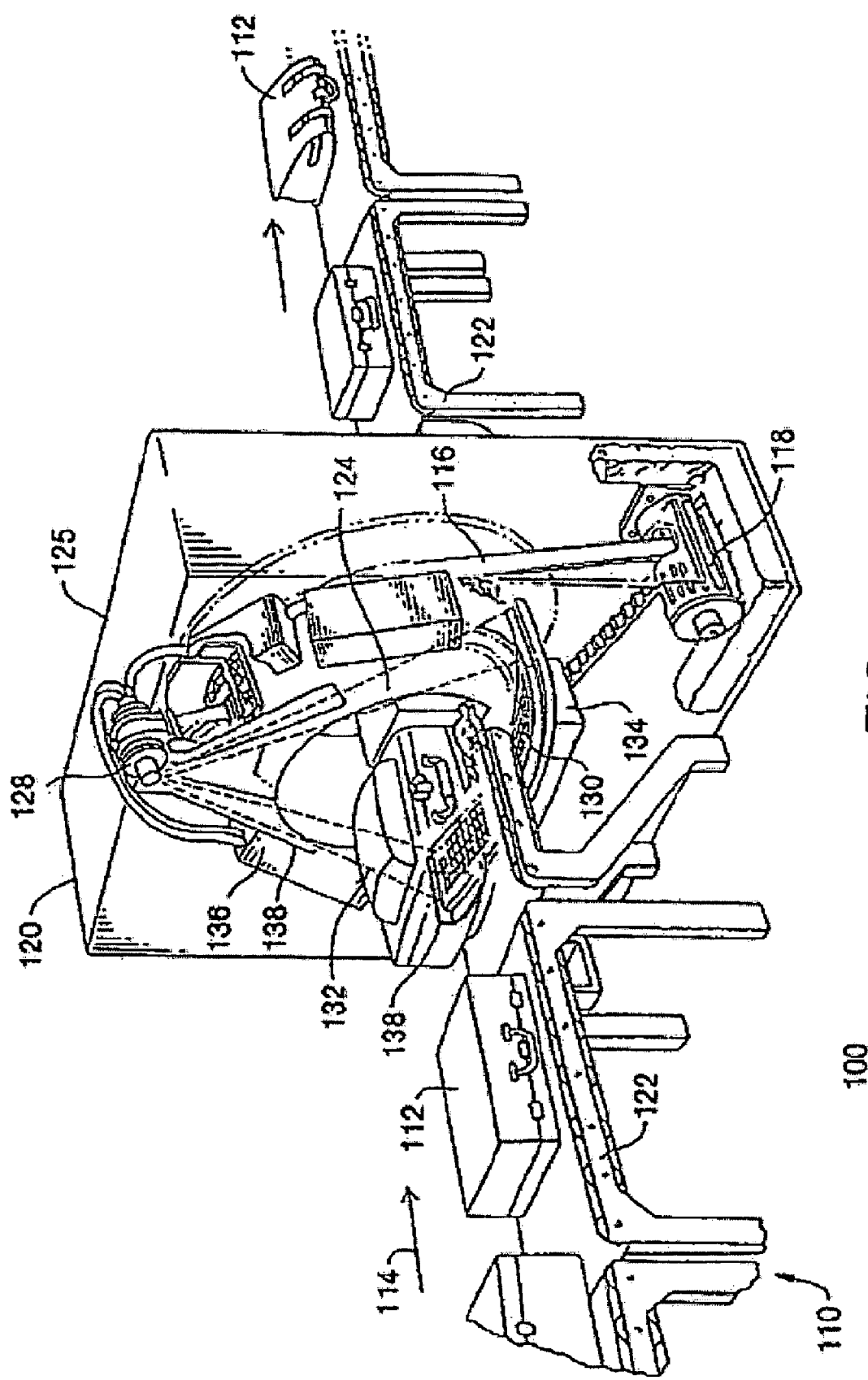
FIG. 1 is a perspective view of a baggage scanning system, known in the prior art.
Figure 6:
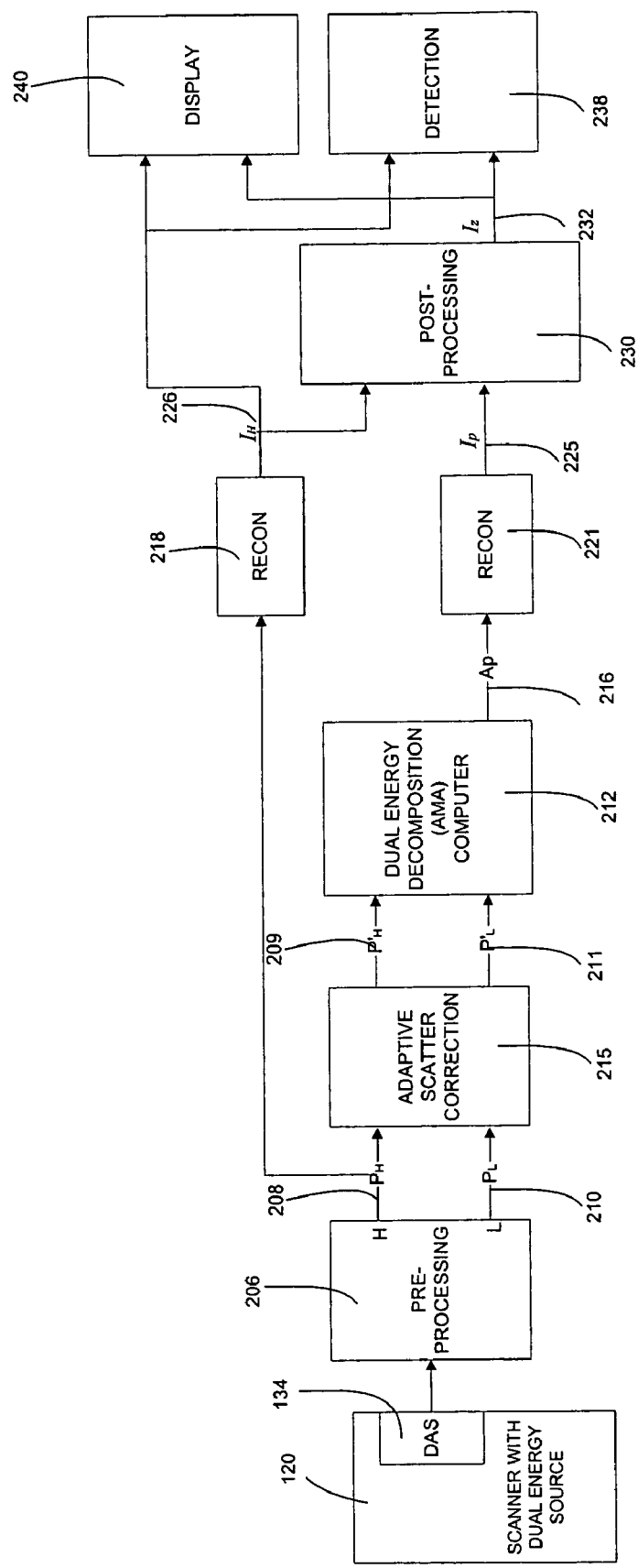
FIG. 6 is a signal flow diagram of a system, like FIG. 5, capable of performing pre-reconstruction analysis according to the teachings of one aspect of the present disclosure.

FIG. 6 illustrates the signal and data flow of the scanner system for explosive detection for the checked baggage for an airport of the present disclosure. Scanner 120 is typically similar to the one shown in FIG. 1 and has an X-ray source capable of producing a fan beam at two distinct energy levels (i.e., dual energy). DAS 134 gathers signals generated by detector array 130 at discrete angular positions of the rotating platform 124, and passes the signals to the pre-processing unit 206. The pre-processing unit 206 re-sorts the data it receives from DAS 134 in order to optimize the sequence for the subsequent mathematical processing. The pre-processing unit 206 also corrects the data from DAS 134 for detector temperature, intensity of the primary beam, gain and offset, and other deterministic error factors associated with each detector of the detector array. Finally, the pre-processing unit 206 extracts data $P_H$ corresponding to high-energy views and routes it to a high energy path 208, and routes the data $P_L$ corresponding to low-energy views to a low energy path 210. The adaptive scatter correction module 215 receives the projection data on the high energy path 208 and the low energy path 210 and performs scatter correction to produce the scatter corrected high energy projections $P'_H$ 209 and scattered corrected low energy projections $P'_L$ 211. The dual energy decomposition computer 212 receives the scatter corrected high energy projections 209 and scattered corrected low energy projections 211 and performs a dual energy decomposition to produce photoelectric projections 216. A first reconstruction computer 221 receives the stream of the photoelectric projection data 216 and generates a photoelectric image $I_p$ 225. The second reconstruction computer 218 receives the stream of high energy projection data $P_H$ 208 and generates a CT image $I_H$ 226. These two images 225 and 226 are processed in the post-processing unit 230 to yield a Z image $I_z$. The unit 240 displays the high energy CT image $I_H$ 226 and the Z image $I_z$ 232 to operators, and the unit 238 uses the Z image 232 and the CT image 226 for automatic explosive detection. In the above system, CT images are used to replace Compton images in computing Z images to reduce the computational cost as described the assignees' co-pending application "Method of and system for computing effective atomic number image in multi-energy computed tomography" by Zhengrong Ying, et. al. U.S. application Ser. No. 10/850,910, filed on May 21, 2004, incorporated herein by reference.

Figure 2:
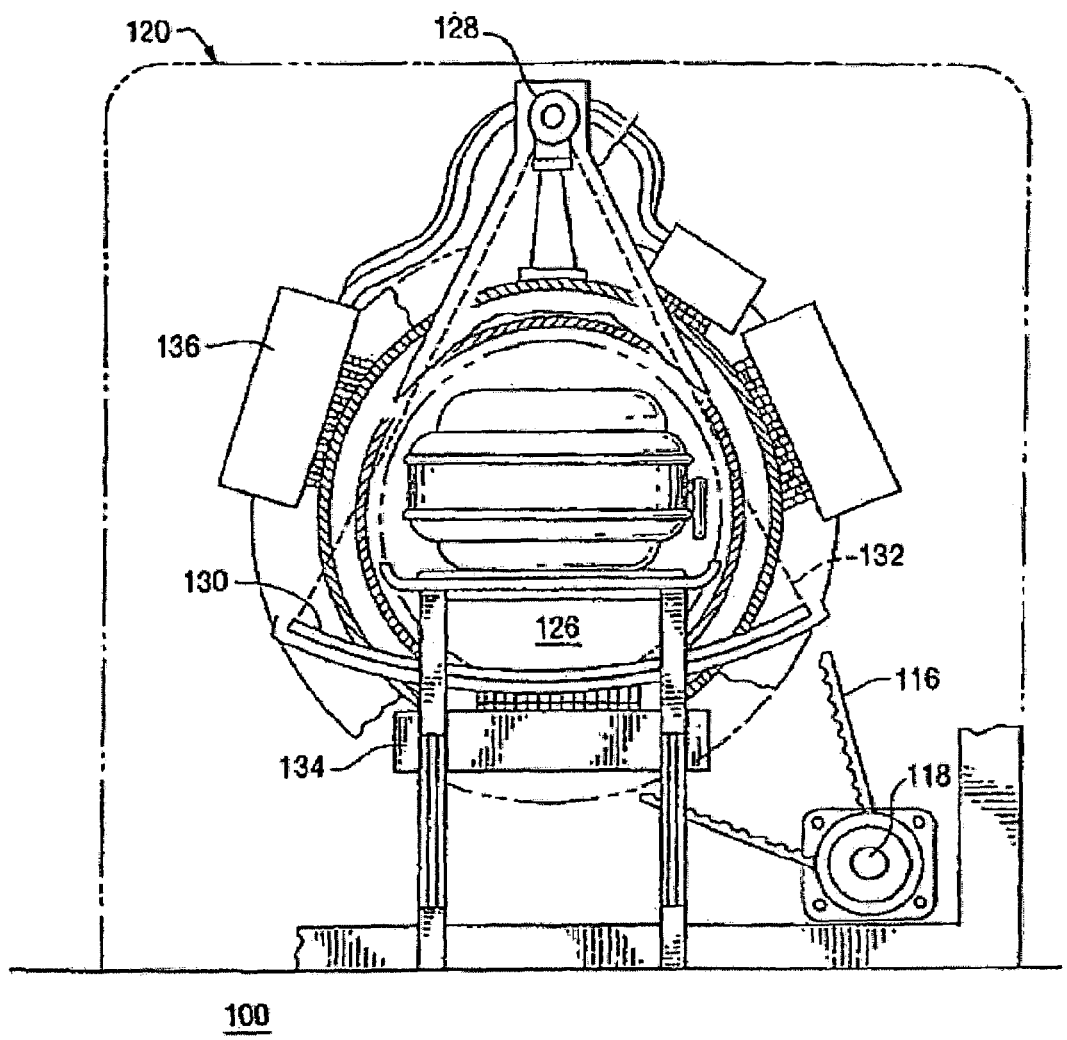
FIG. 2 is a cross-sectional end view of the system of FIG. 1.
Figure 3:
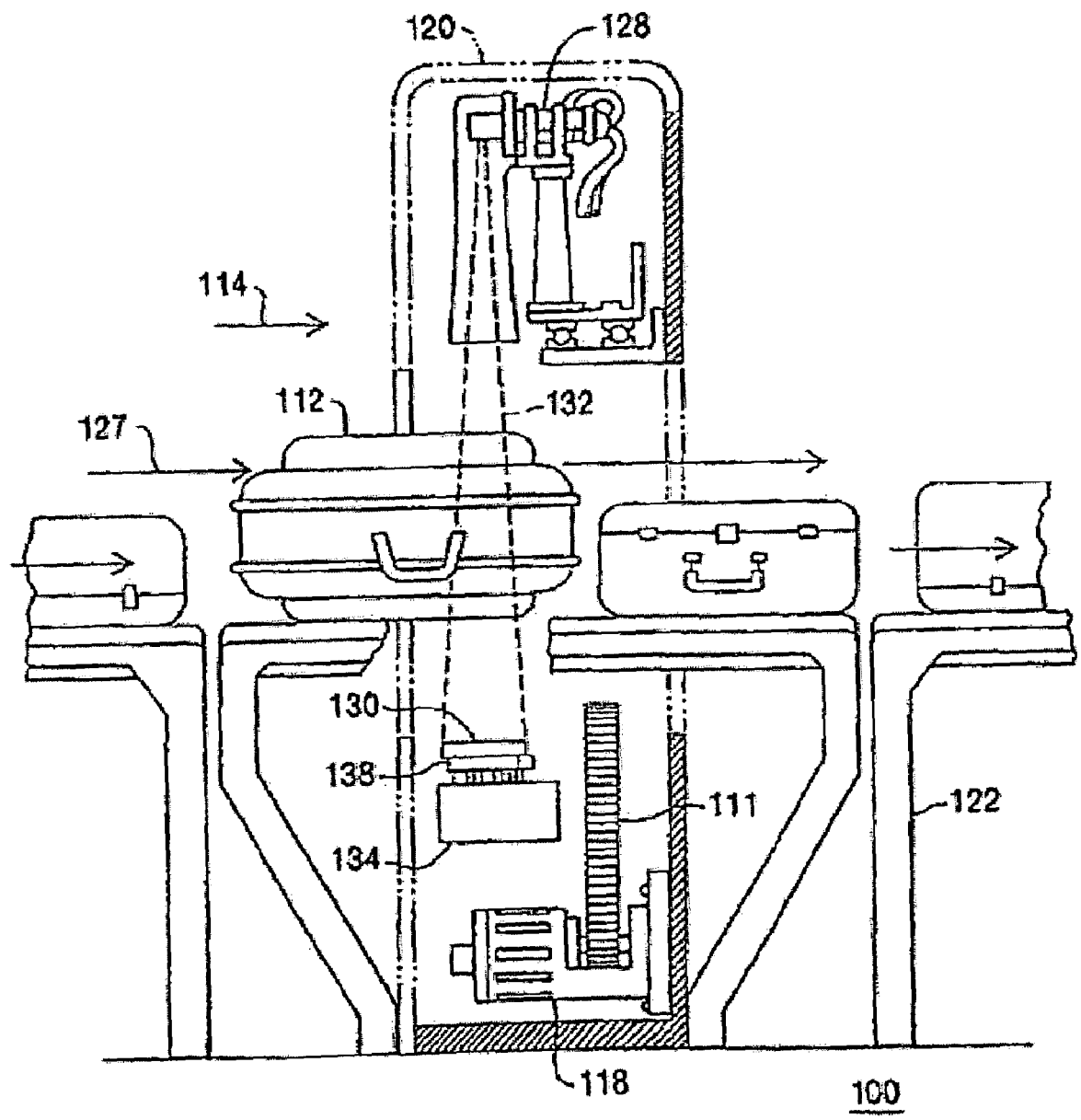
FIG. 3 is a cross-sectional radial view of the system of FIG. 1.
Figure 4:
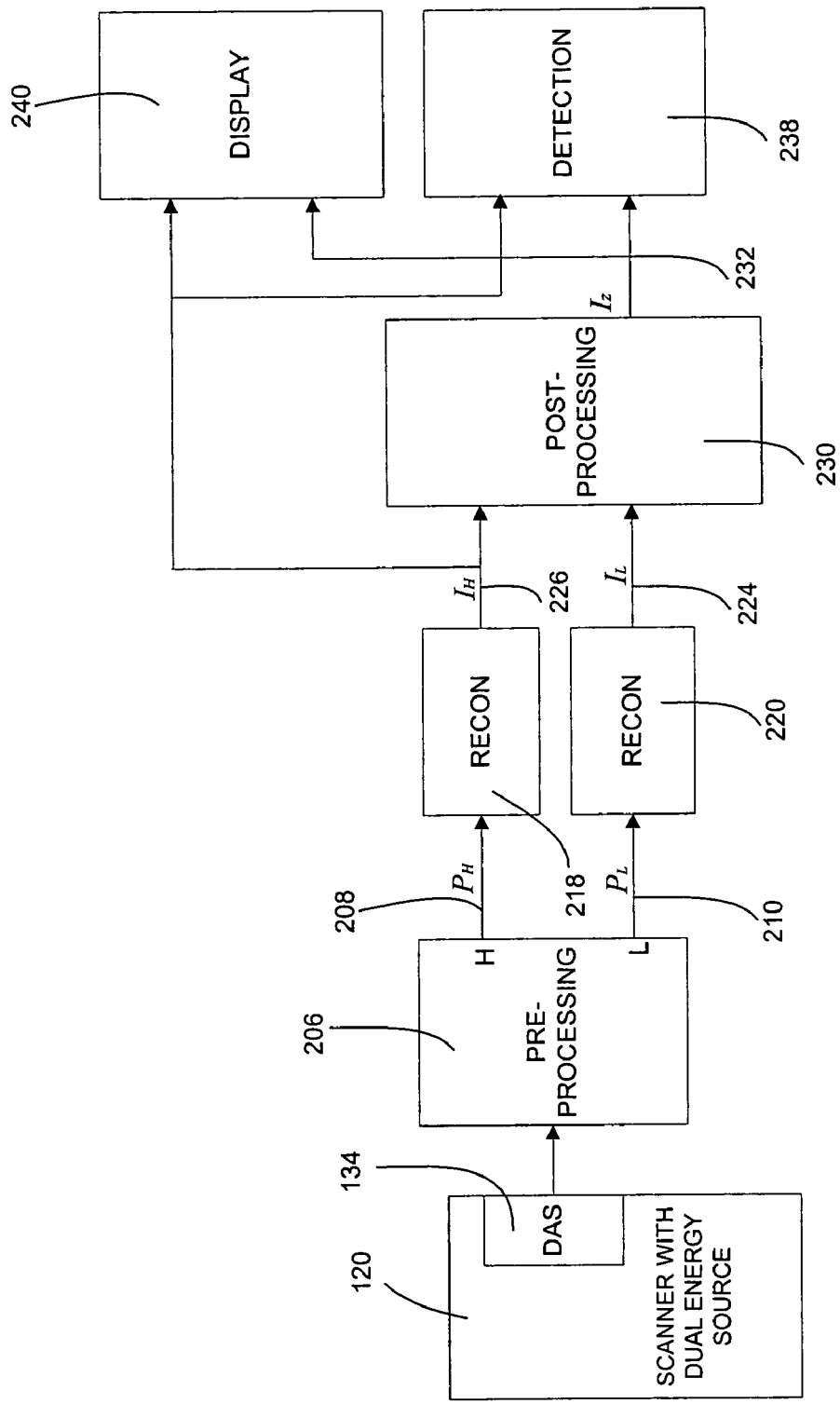
FIG. 4 is a signal flow diagram of a prior art system capable of performing post-reconstruction analysis.
Figure 5:
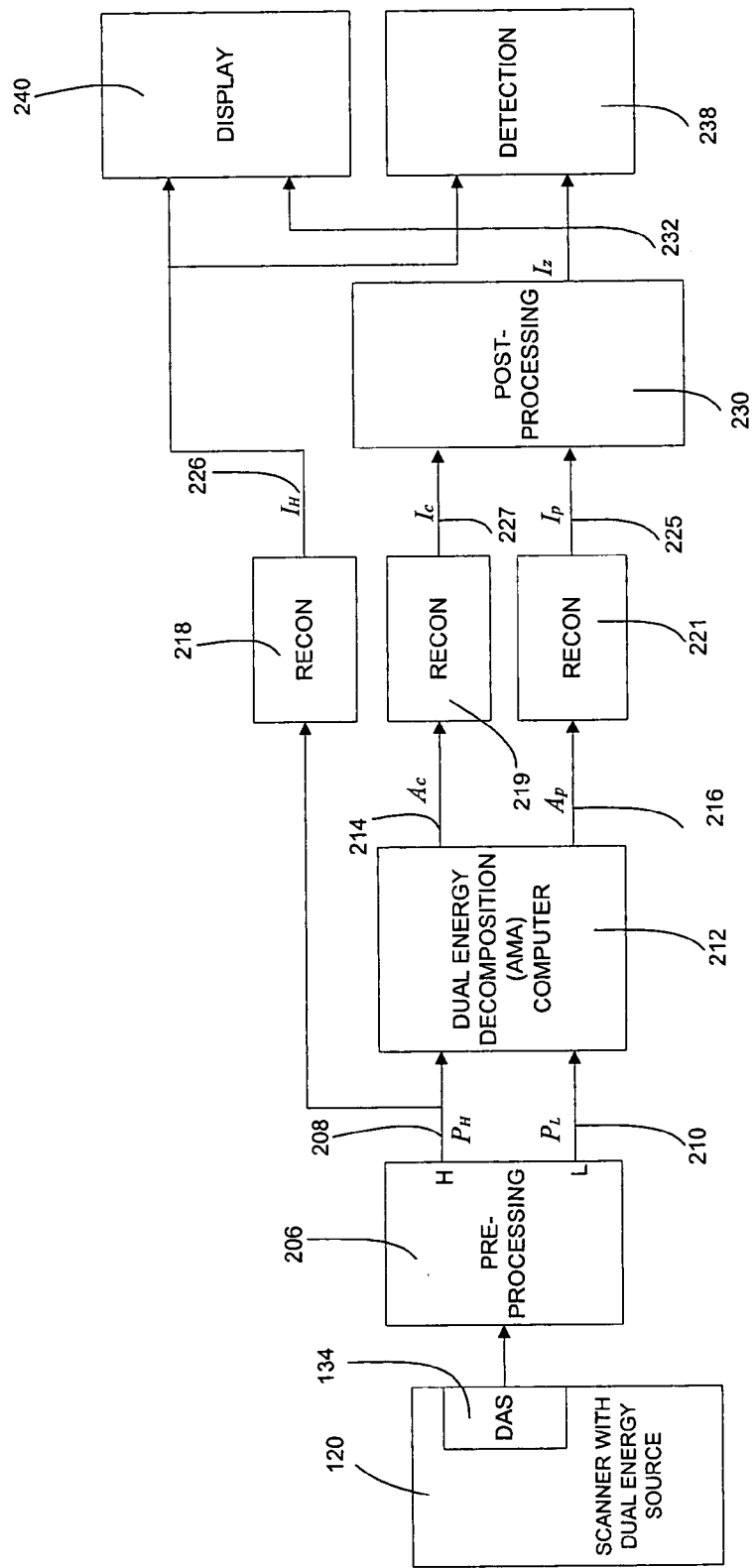
FIG. 5 is a signal flow diagram of a prior art system capable of performing pre-reconstruction analysis.
Figure 7:
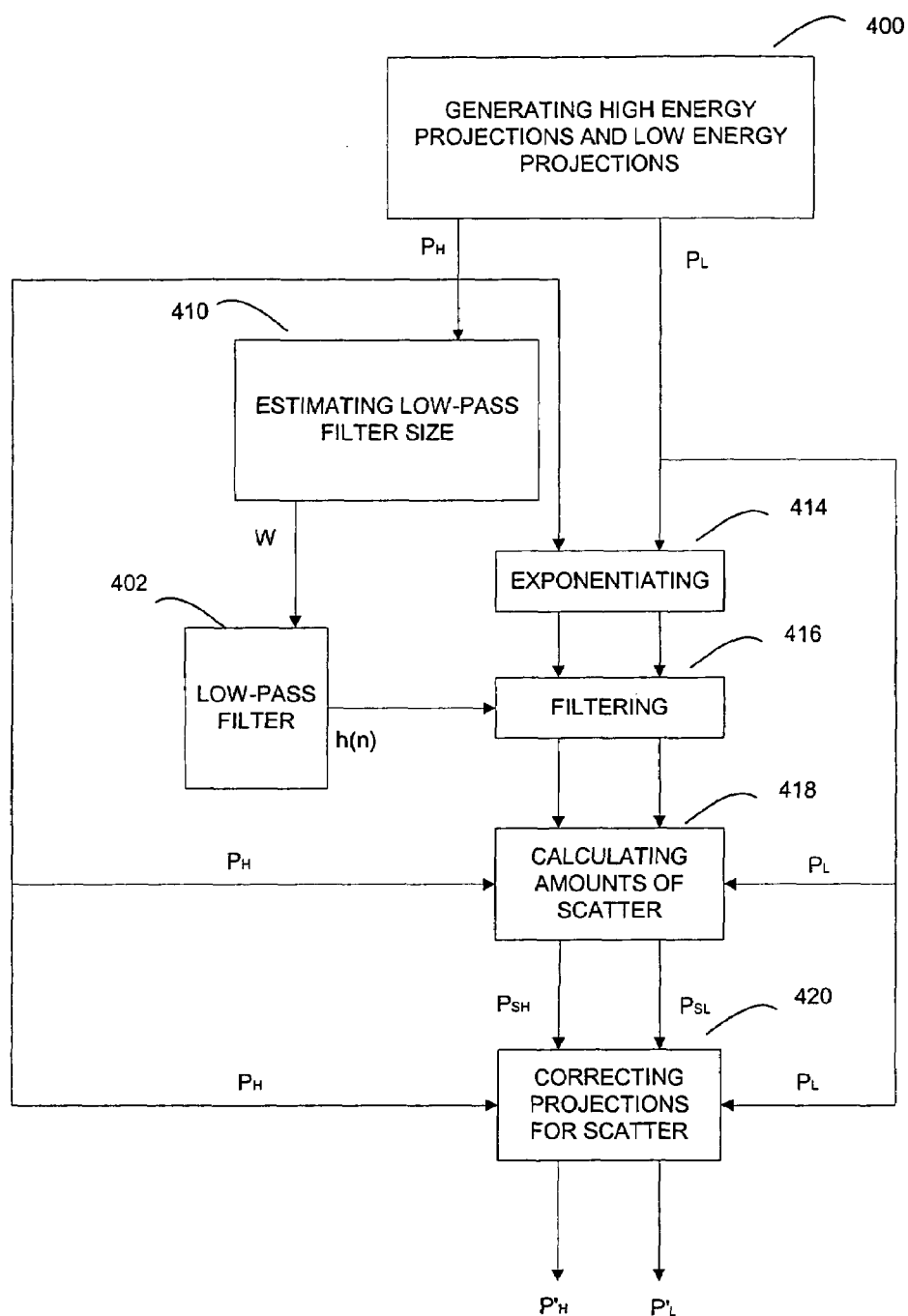
FIG. 7 contains a top-level flow diagram which illustrates the logical flow of one embodiment of adaptive scatter correction for multi-energy projection data in accordance with the teachings of the present disclosure.

In accordance with one aspect of the present disclosure, an adaptive scatter correction algorithm for multi-energy projection data acquired by scanning a set of objects using at least two X-ray spectra is provided. The input projection data may include a set of high energy projections and a set of low energy projections. This embodiment is described with respect to a CT scanner with an x-ray source and detector configuration, such as that shown and described with respect to FIGS. 1, 2, and 3. In accordance with one aspect of the present disclosure, a low-pass filter of variable size is also provided for estimating the amounts of scatter for both sets of projections, where the size is determined adaptively depending on the input projection data. The present disclosure for adaptive scatter correction comprises:

Estimating the size of the low-pass filter from the set of high energy projections, Computing amounts of scatter for both sets of projections using the low-pass filter of the estimated size Correcting both sets of projections with the computed amounts of scatter FIG. 7 contains the flow chart of a preferred embodiment of the method in accordance with one aspect of the present disclosure, and is used preferably to describe the details of the method. At step 400, the scanner source generates a low energy spectrum and a high energy spectrum. The detector array containing a matrix of detectors receives the corresponding high energy and low energy x-ray intensities.

Figure 8:
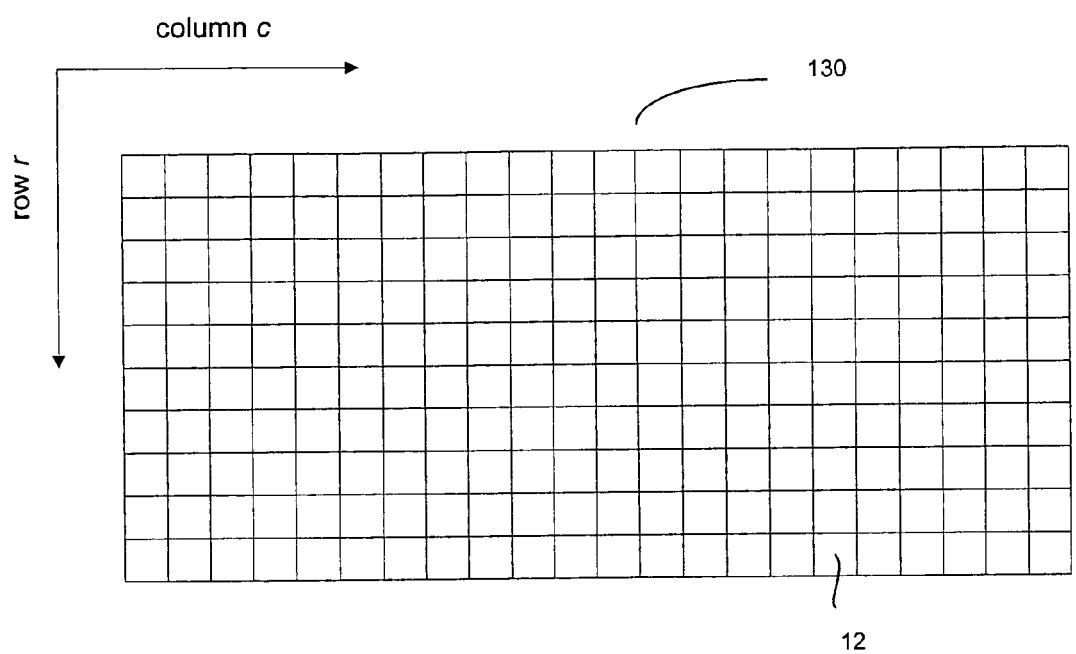
FIG. 8 illustrates an example of a detector array of the present disclosure.

FIG. 8 shows a useful pattern of a detector array 130 comprising of a matrix of detectors 12 of the present disclosure. Denote $c(0, \ldots, S-1)$ as the index of the column of detector array shown as the horizontal direction in FIG. 8. $I_L(c)$ and $I_H(c)$ are the corresponding x-ray intensities that are detected when the object is scanned. $I_{OL}(c)$ and $I_{OH}(c)$ are the corresponding x-ray intensities that are detected in the absence of any object. $P_L(c)$ and $P_H(c)$ are the corresponding low and high energy projections that are measured by the scanner's detector at a given angle, given by:

$$P_L(c) = -\ln\left(\frac{I_L(c)}{I_{OL}(c)}\right)$$

$$P_H(c) = -\ln\left(\frac{I_H(c)}{I_{OH}(c)}\right)$$

Note that there are typically more well-known steps involved in correcting the above computed $P_L$ and $P_H$ to yield satisfactory image quality.

In one embodiment a one-dimensional odd-number-point long rectangular low-pass filter is provided at step 402. The filter with the following form is preferably used, $$h(n) = \frac{1}{2W+1}, n = 0, \ldots 2W$$

where W is the filter size, and is estimated from the input projection data.

At step 410, the filter size is estimated using the high energy projections as described below. First, the high energy projections $P_H(c)$ are thresholded into binary projections $B(c)$ as follows, $$B(c) = \begin{cases} 0, & \text{if } P_H(c) < P_{shape} \\ 1, & \text{otherwise} \end{cases}$$

where $P_{shape}$ is a pre-defined threshold, and its value is experimentally determined, for example, $P_{shape}=1.5$ yields satisfactory results in the assignee's scanner system as described before.

The binary projections B(c) are then filtered using a rectangular window with a pre-defined size of $W_{ini}$ as follows, $$C(c) = \sum_{n=0}^{2W_{ini}} B(c+n-W_{ini})$$

The pre-defined value of $W_{ini}$ is experimentally determined, for example, $W_{ini}=40$ yields satisfactory results in the assignee's scanner system as described before. Note that zero-padding scheme is preferably used for the boundary conditions, i.e., C(c)=0, for c<0 and c≧S.

The maximum value from the filtered binary projections is obtained as follows, $$M = \max_{c \in \{0,\ldots,S-1\}} C[c]$$

The filter size is calculated as follows from the maximum value of the filtered binary projections as follows, $$W' = \left\lfloor \frac{\sigma_w M W_{ini}}{2W_{ini}+1} + \frac{1}{2} \right\rfloor$$

where $\sigma_w$ is pre-defined constant, and the value is experimentally determined. For example, $\sigma_w=1.4$ yields satisfactory results in the assignee's scanner as described before. Note that $\lfloor x \rfloor$ is the maximum integer which is not greater than x.

Finally, at step 402 the calculated filter size W' is clamped with a pre-defined value $W_{min}$ to yield the estimated filter size W for estimating amounts of scatter as follows, $$W = \begin{cases} W_{min}, & \text{if } W' < W_{min} \\ W', & \text{otherwise} \end{cases}$$

Note that the value of $W_{min}$ is experimentally determined, for example, $W_{min}=10$ yields satisfactory results in the assignee's scanner system as described before.

Figure 9:
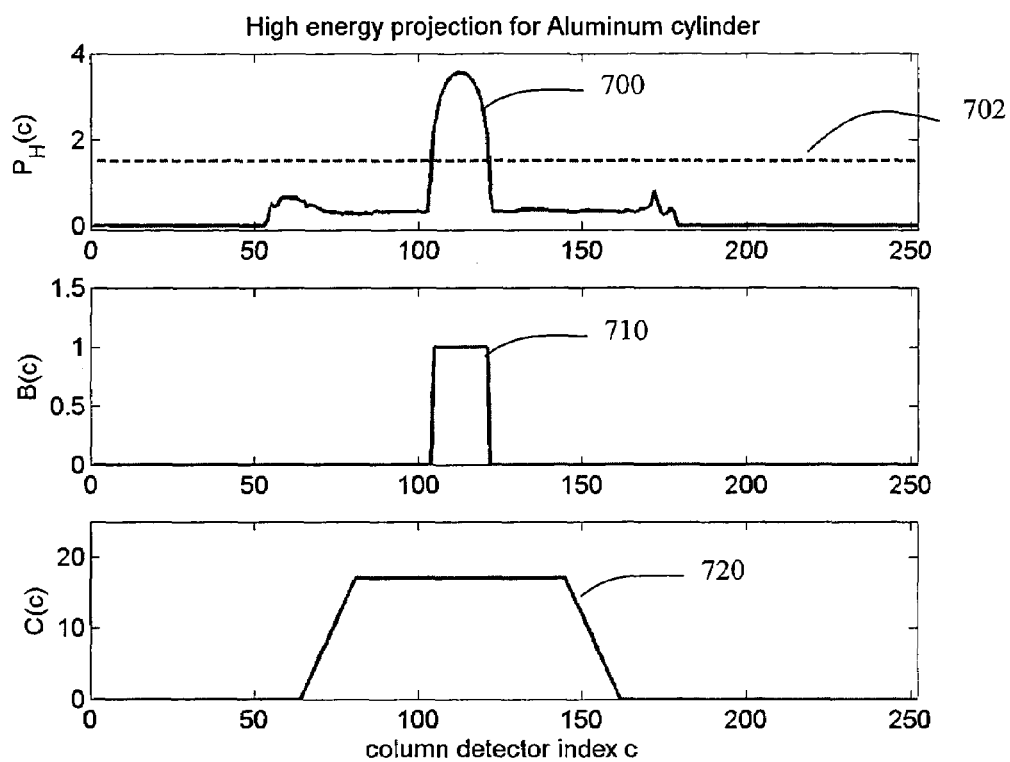
FIG. 9 shows a graphical illustration of high energy projections of an Aluminum cylinder for one row of a detector array, and intermediate results for estimating the low-pass filter size.
Figure 10:
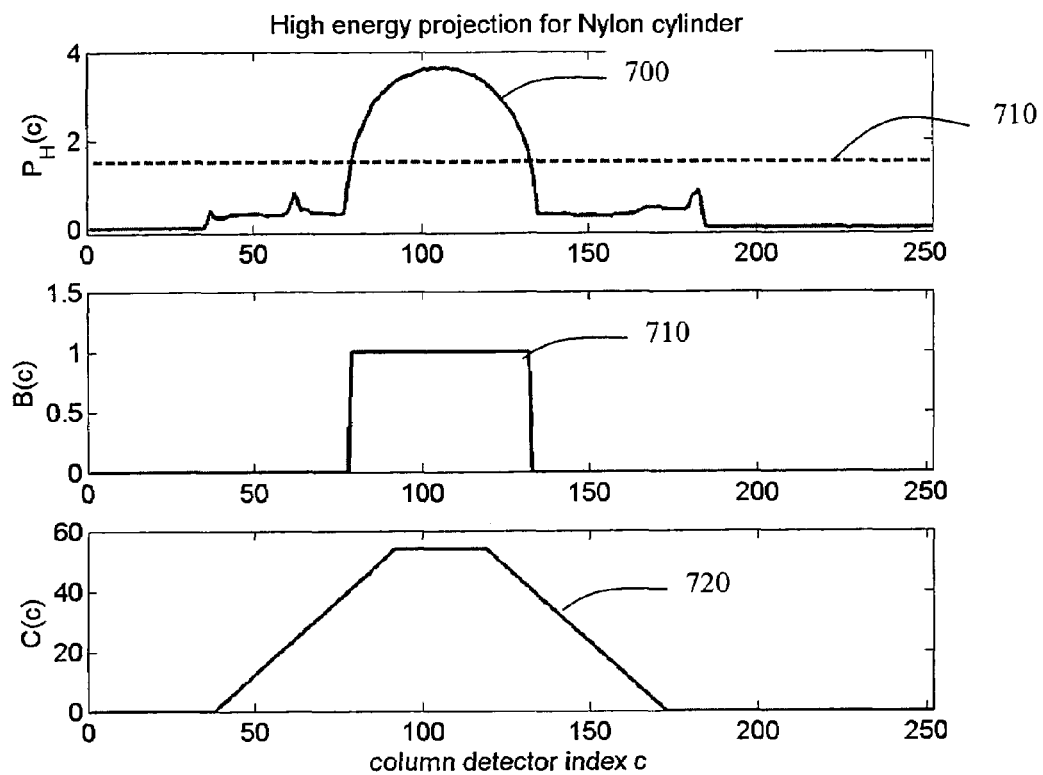
FIG. 10 shows a graphical illustration of high energy projection of a Nylon cylinder for one row of a detector array, and intermediate results for estimating the low-pass filter size.

FIG. 9 and FIG. 10 show respectively examples of high energy projection data of an Aluminum cylinder and a Nylon cylinder for one row detectors of a detector array. Note that the Aluminum cylinder and Nylon cylinder have different diameters and different projection data values. In the example, the estimated filter size W for the Nylon cylinder is 37, and is 12 for the Aluminum cylinder, indicating that the algorithm is adaptive to the size and attenuation of the scanned objects. In the example of both FIG. 9 and FIG. 10, item 700 is the high energy projections; item 702 is $P_{shape}$ at value of 1.5; item 710 is the binary projection B(c); and item 720 is the filtered binary projection C(c).

Referring again to FIG. 7, at step 414, the high energy projections and low energy projections are exponentiated as follows, $$Q_H(c) = \exp(P_H(c)),$$

$$Q_L(c) = \exp(P_L(c)),$$

Next at step 416, filtering is performed on the exponentiated projections using the low-pass filter h(n) with the estimated filter size W as follows, $$F_H(c) = \sum_{n=0}^{2W} h(n) Q_H(c+n-W)$$

$$F_L(c) = \sum_{n=0}^{2W} h(n) Q_L(c+n-W)$$

Note that the border replication scheme is used to extend the projection data to its index limits, i.e., $Q_H(c) = Q_H(0)$, and $Q_L(c) = Q_L(0)$ for $c<0$, $Q_H(c) = Q_H(S-1)$, and $Q_L(c) = Q_L(S-1)$ for $c \geq S$ At step 418, the amounts of scatter are calculated as follows, $$P_{SH}(c) = -\alpha_H P_H(c) F_H(c)$$

$$P_{SL}(c) = -\alpha_L P_L(c) F_L(c)$$

Note that $\alpha_H$ and $\alpha_L$ are pre-defined constants, $\alpha_L$ is preferably larger than $\alpha_H$ due to the fact that the low energy projections have more scatter than the high energy projections. The values are experimentally determined, for example, $\alpha_H=0.010$ and $\alpha_L=0.015$ yield satisfactory results in the assignee's scanner system as described before.

At step 420, the amounts of scatter are subtracted from the input projections to yield the corrected projections. Denote $P'_H(c)$ as the scatter corrected high energy projections, and $P'_L(c)$ as the scatter corrected low energy projections, which are calculated as follows, $$P'_H(c) = P_H(c) - P_{SH}(c)$$

$$P'_L(c) = P_L(c) - P_{SL}(c)$$

While this disclosure has been particularly shown and described with references to preferred embodiments thereof, it will be understood by those skilled in the art that various changes in form and details may be made therein without departing from the spirit and scope of the disclosure as defined by the following claims. Such variations include using low energy projections for estimating the filter size, using two-dimensional filters over the detector array or using three-dimensional filters over the detector array and view index, using other types of low-pass filters, and skipping the exponentiating step in calculating amounts of scatter.

The invention claimed is:

1. A method of adaptive scatter correction in the absence of scatter detectors for the input projection data in multi-energy X-ray computed tomography, wherein the input projection data include a set of low energy projections and a set of high energy projections acquired by scanning a set of objects using at least two x-ray spectra, wherein a low-pass filter of variable size is provided, comprising:

A. Estimating the filter size of the low pass filter as a function of the input projection data, including:
- A1. Thresholding at least one set of projections into binary projections;
- A2. Filtering the binary projections;
- A3. Finding maximum of the filtered binary projections:
- A4. Calculating the filter size from the maximum found in A3;

B. Computing amounts of scatter in the input projection data using the low-pass filter with the calculated filter size from A4;

C. Correcting the input projection data for the scatter using the amounts of scatter computed from B.

2. The method of claim 1, wherein C includes subtracting the computed amounts of scatter from both sets of projections to yield scatter corrected projections.

3. The method of claim 1, wherein the low-pass filter may be a one-dimensional odd-number-point long rectangular filter so that the estimating step A includes estimating the filter size of such a filter.

4. The method of claim 1, wherein A includes using high energy projections for estimating the filter size.

5. The method of claim 1, wherein A includes setting the calculated filter size to a pre-defined maximal value if the calculated filter size exceeds the predefined maximal value.

6. A method of adaptive scatter correction in the absence of scatter detectors for the input projection data in multi-energy X-ray commuted tomography, wherein the input projection data include a set of low energy projections and a set of high energy projections acquired by scanning a set of objects using at least two x-ray spectra, wherein a low-pass filter of variable size is provided, comprising:

A. Estimating the filter size of the low pass filter as a function of the input projection data;

B. Computing amounts of scatter in the input projection data using the low-pass filter with the estimated filter size from A, including:
- B1. Exponentiating both sets of projections so as to provide exponentiated projections;
- B2. Filtering the exponentiated projections with the estimated filter size;
- B3. Computing amounts of scatter from the filtered projections; and C. Correcting the input projection data for the scatter using the amounts of scatter computed from B3.

7. The method of claim 6, wherein B3 includes multiplying the filtered projections with a larger scale factor for low energy projections and a smaller scale factor for high energy projections.

8. A system for adaptive scatter correction in the absence of scatter detectors for the input projection data in multi-energy X-ray computed tomography, wherein the input projection data may include a set of low energy projections and a set of high energy projections acquired by scanning a set of objects using at least two x-ray spectra, wherein a low-pass filter of variable size is provided, comprising:

A. A subsystem constructed and arranged so as to estimate the filter size of the low-pass filter as a function of the input projection data, including:
- A1. A module constructed and arranged so as to threshold one set of projections into binary projections;
- A2. A module constructed and arranged so as to filter the binary projections;
- A3. A module constructed and arranged so as to find maximum of the filtered binary projections;
- A4. A module constructed and arranged so as to calculate the filter size from the maximum found by the module of A3.

B. A subsystem constructed and arranged so as to compute amounts of scatter in the input projection data using the low-pass filter with the calculated filter size from the module of A4;

C. A subsystem constructed and arranged so as to correct the input projection data for scatter using the amounts of scatter computed from the subsystem of B.

9. The system of claim 8, wherein subsystem C includes a subtractor constructed and arranged so as to subtract the computed amounts of scatter from both sets of projection data so as to yield scatter corrected projections.

10. The system of claim 8, wherein the low-pass filter may be a one-dimensional odd-number-point long rectangular filter.

11. The system of claim 8, wherein said subsystem is constructed and arranged so as to estimate the filter size of the low-pass filter as a function of the high energy input projection data.

12. The system of claim 8, wherein said module A4 includes a feature for setting the calculated filter size to a pre-defined maximal value if the calculated filter size exceeds the pre-defined maximal value.

13. A system for adaptive scatter correction in the absence of scatter detectors for the input projection data in multi-energy X-ray computed tomography, wherein the input projection data may include a set of low energy projections and a set of high energy projections acquired by scamming a set of objects using at least two x-ray spectra, wherein a low-pass filter of variable size is provided, comprising:

A. A subsystem constructed and arranged so as to estimate the filter size of the low-pass filter as a function of the input projection data;

B. Computing amounts of scatter in the input projection data using the low-pass filter with the estimated filter size from the subsystem of A, including:
- B1. A module constructed and arranged so as to exponentiate both sets of input projection data;
- B2. A module constructed and arranged so as to filter the exponentiated projections with the estimated filter size;
- B3. A module constructed and arranged so as to compute amounts of scatter from the filtered projection data; and C. A subsystem constructed and arranged so as to correct the input projection data for scatter using the amounts of scatter computed by the module of B3.

14. The system of claim 13, wherein said module B3 includes a multiplier constructed and arranged so as to multiply the filtered projections with a larger scale factor for low energy projections and a smaller scale factor for high energy projections.

* * * * *